US00PP12264P2

(12) United States Plant Patent
McGranahan et al.

(10) Patent No.: US PP12,264 P2
(45) Date of Patent: Dec. 11, 2001

(54) PERSIAN WALNUT TREE NAMED 'ROBERT LIVERMORE'

(75) Inventors: Gale McGranahan; Charles Leslie; Herbert A. Phillips, all of Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/475,028

(22) Filed: Dec. 30, 1999

(51) Int. Cl.[7] ..... A01H 5/00
(52) U.S. Cl. ..... Plt./154
(58) Field of Search ..... Plt./154

*Primary Examiner*—Bruce R. Campell
*Assistant Examiner*—Annette H Para
(74) *Attorney, Agent, or Firm*—Burns, Doane, Swecker & Mathis, L.L.P.

(57) ABSTRACT

A new and distinct Persian Walnut Tree (i.e., *Juglans regia*) is provided. Jumbo walnuts are produced having thick well-filled hulls. There is little walnut size variation in a given harvest. The kernels are easy to remove and display a distinctive atypical red-purple pellicle. The resulting walnut crop commonly can be harvested from a young tree prior to that of the 'Chandler' cultivar U.S. Plant Pat. No. 4,388) at Davis, Calif. The walnut kernels in view of their distinctive naturally-occurring festive red-purple pellicle are particularly suited for consumption at parties, holidays, or other special occasions.

3 Drawing Sheets

SUMMARY OF THE INVENTION

The new *Juglans regia* Walnut Tree of the present invention was created at Davis, Calif. during 1991 by a controlled cross of the 'Howard' cultivar U.S. Plant Pat. No. 4,405) and the 'Purpurea' cultivar (non-patented in the United States). See U.S. Plant Pat. No. 4,405 for the ancestry of the 'Howard' parent. The 'Purpurea' parent used in the cross also identified as 'RX1088' and was obtained from the Walnut collection of E. Germain (Institut National de la Recherche Agronomique, Station de Recherches d'Arboriculture Fruitiere, Bordeaux, France). The Kernels of the 'Howard' parent bear a typical seed coat that is amber or light amber. The kernels of the 'Purpurea' cultivar possess a reddish-brown seed coat. The parentage of the new cultivar can be summarized as follows:

'Howard'×'Purpurea'.

Seeds from the cross were collected and planted and the resulting trees were carefully observed. A single plant of the new cultivar was selected in view of its highly distinctive combination of characteristics. This selection initially was designated '91-75-15'.

It was found that the new *Juglans regia* cultivar of the present invention exhibits the following combination of characteristics:

(a) Forms jumbo-sized walnuts with little size variation in a given harvest which possess strong thick well-filled shells and easy to remove kernels, (b) Forms kernels which display a distinctive red-purple pellicle, (c) Bears fruit laterally, and (d) Yields a walnut crop that commonly can be harvested from a young tree prior to that of the 'Chandler' cultivar (U.S. Plant Pat. No. 4,388) at Davis, Calif.

The new cultivar of the present invention has been propagated by grafting at Davis, Calif. on 'Paradox' hybrid rootstock. The distinctive characteristics of the new cultivar have been found to be stable and are transmitted from one generation to another following such a sexual propagation.

The new cultivar of the present invention has been named the 'Robert Livermore' cultivar. Rober Livermore was a supporter of the Walnut Improvement Program at the University of California for many years and is honored through the naming of this plant.

BRIEF DESCRIPTION OF THE PHOTOGRAPHS

The accompanying photographs show, as true as is reasonably possible to make the same in color illustrations of this character typical illustrations of the new cultivar of the present invention while grafted on 'Paradox' hybrid rootstock. The trees were three years of age and were grown at Davis, Calif. The trees of FIGS. 1, 2 and 3 were grafted during the Spring of 1998 and were photographed during November, 1999.

Figure 1:
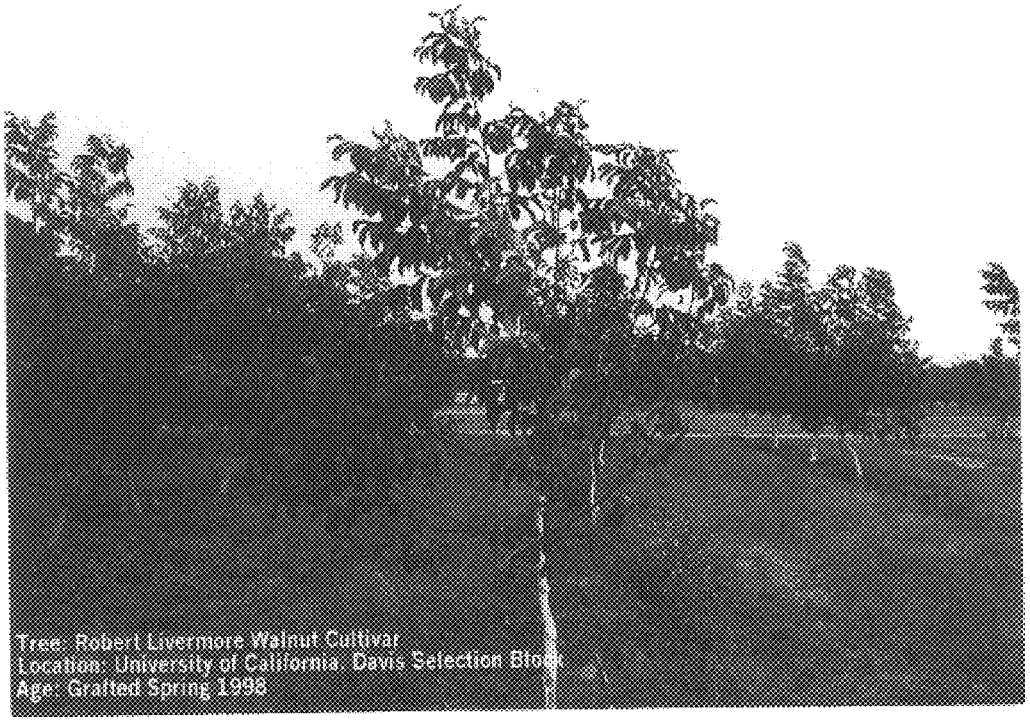

FIG. 1—shows a typical young trees of the 'Robert Livermore'cultivar where the trunk portions of the trees have been whitewashed to minimize sun damage.

Figure 2:
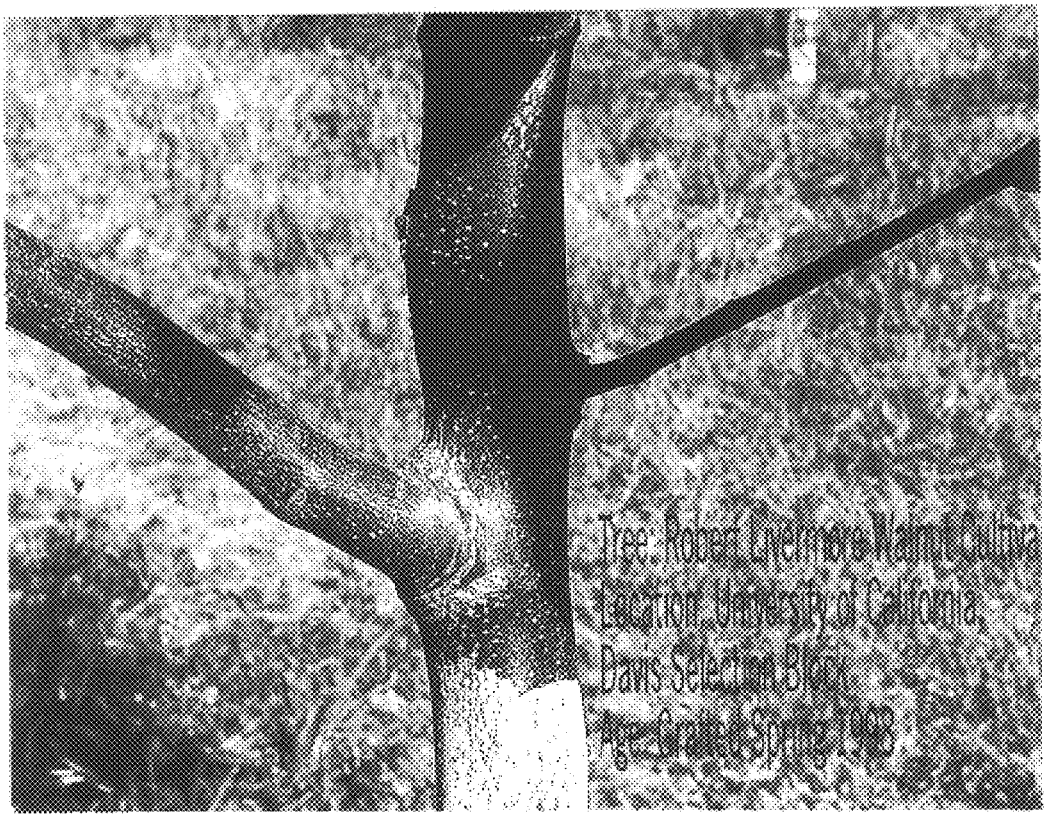

FIG. 2—shows a near view of the typical trunk and lateral branches of the 'Robert Livermore' cultivar. The lower trunk portion has been painted white.

Figure 3:
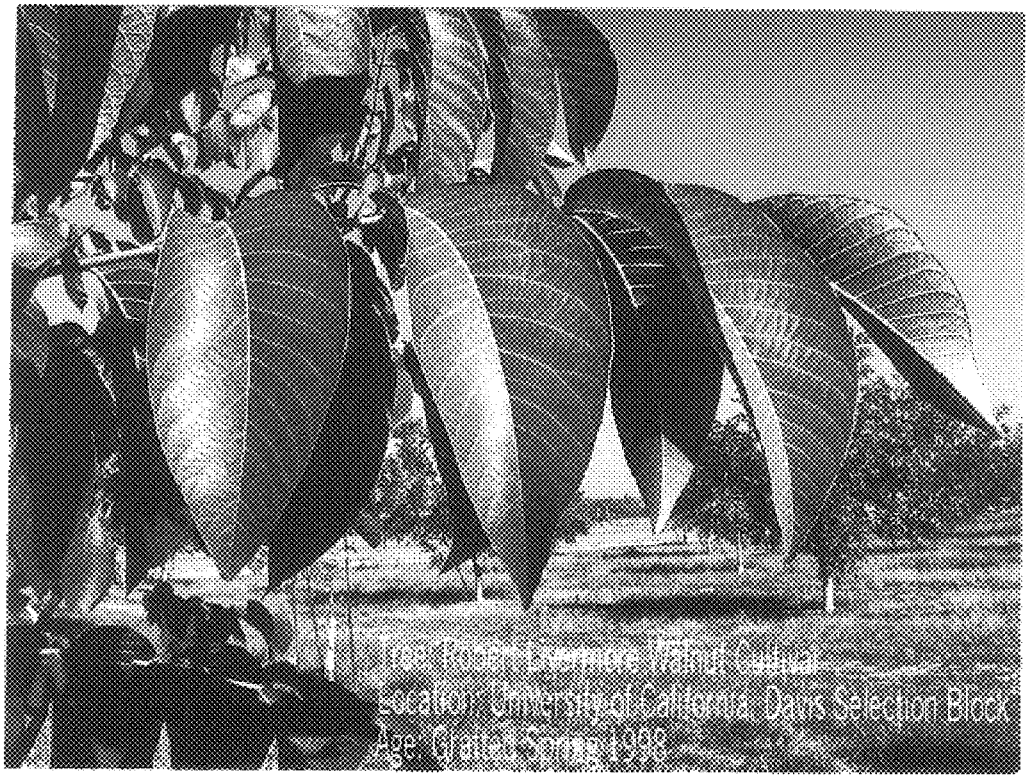

FIG. 3—shows a near view of typical leaves and stem of the 'Robert Livermore' cultivar.

Figure 4:
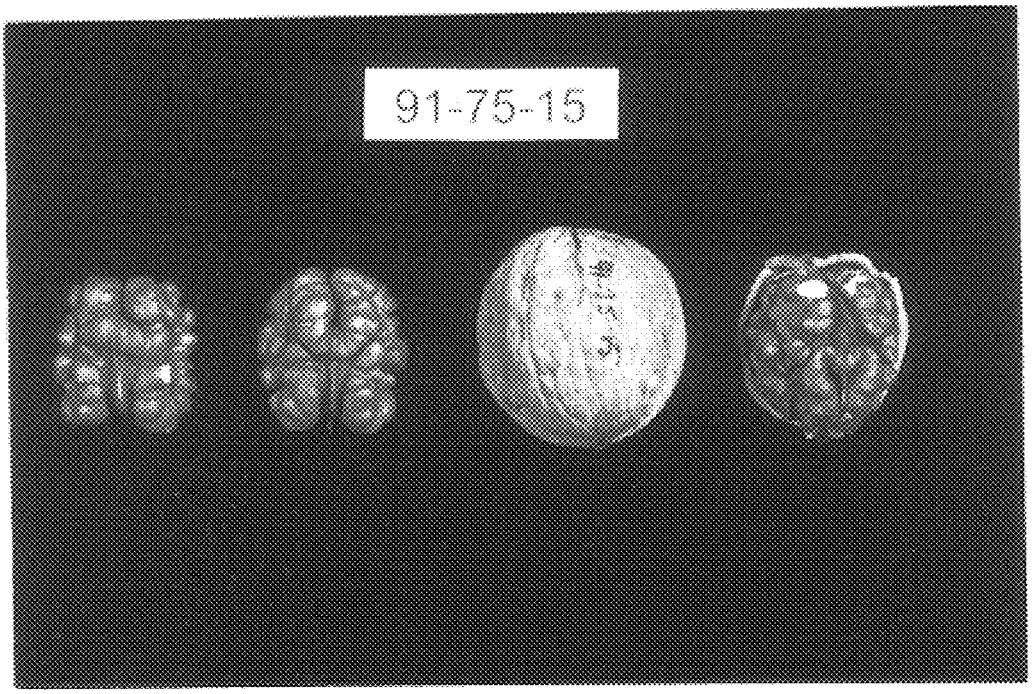

FIG. 4—shows typical views of the walnuts of new cultivar. From left to right are shown two kernel halves, a walnut in the shell, and a walnut in the shell wherein half of the shell has been removed. The photograph was prepared during March 1998 while observing the walnut harvest from the previous growing season. The distinctive red-purple pellicle is readily apparent once the shell is removed.

Figure 5:
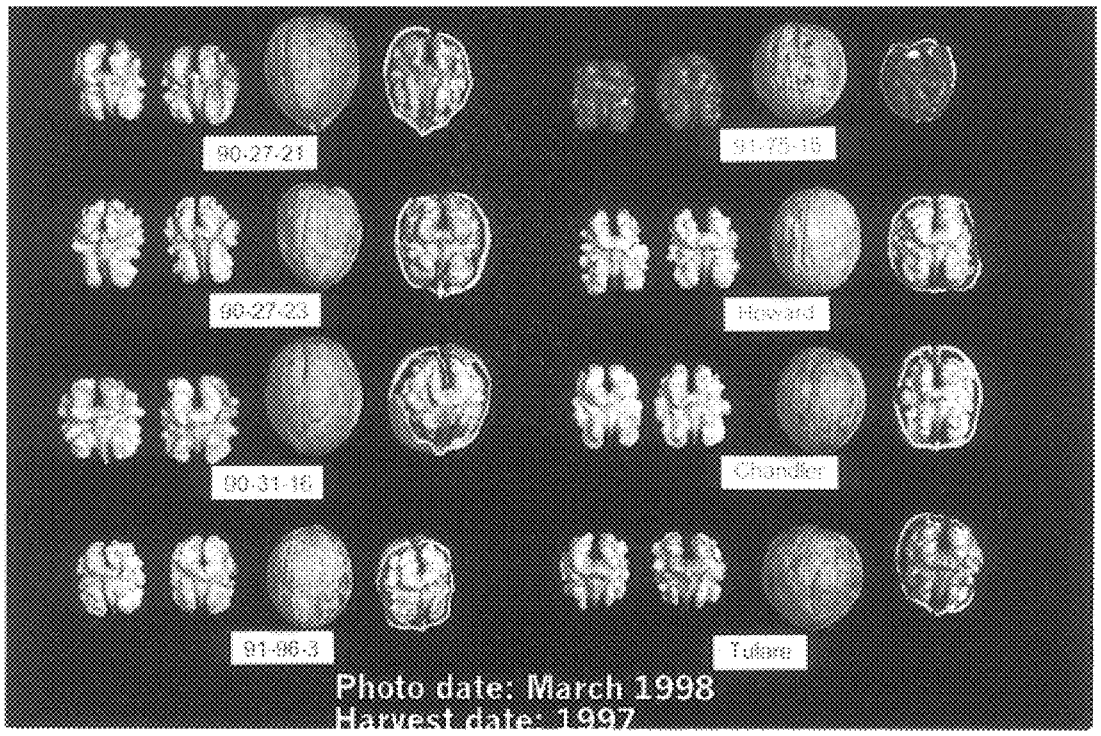

FIG. 5—again presents at the upper right the subject matter of FIG. 4 and includes for comparative purposes similar views of four non-released and non-patented experimental varieties '90-27-21', '90 -27-23', '90-31-16' and '91- 96-3', the 'Howard' cultivar (U.S. Plant Pat. No. 4,405), the 'Chandler' cultivar (U.S. Plant Pat. No. 4,388), and the 'Tulane' cultivar U.S. Plant Pat. No. 8,268).

DETAILED DESCRIPTION

The description is based upon Walnut Trees propagated by grafting on 'Paradox' hybrid rootstock and growing in the field at Davis, Calif.

The Munsell color chart is used in the identification of color. Also, common color terms are to be accorded their ordinary dictionary significance.

Botanical classification: *Juglans regia*, 'Robert Livermore'.

*Female parent.*—'Howard' cultivar (U.S. Plant Pat. No. 4,405).

*Male parent.*—'Purpurea' (non-patented in the United States).

Plant: The growth habit of the tree is illustrated in FIGS. 1 and 2. A three year-old tree typically displays a height of approximately 18 feet and a canopy diameter of approximately 10 feet. The trunk diameter at 4 feet above the ground is approximately 60 mm. The bark (as illustrated) is typical of *Juglans regia*. The young bark is smooth and dark brown (5.5 YR 3.5/1.8 gy. yBr.) with numerous raised white lenticels. The mature bark is smooth and gray (6.7Y 7.4/0.2 1.Gy.) with few lenticles and some cream-colored vertical marking. On one to two year-old bark there commonly are approximately 10 lenticels per square cm that are approximately 0.5 to 3.5 mm in size and 9.7YR 6.4/2.5 1.gy.yBr. in coloration.

Foliage: The attractive dark green foliage is illustrated in FIG. 3 and is typical of *Juglans regia*. Leaf out has occurred approximately the same time as the 'Chandler' cultivar (U.S. Plant Pat. No. 4,388). Leaf out for young trees of the new cultivar during 1994 to 1998 has occurred on April 5th on average. For comparative purposes the 'Chandler' cultivar leafed out on April 3rd on average from 1988 to 1998. The leaf out for young trees of the new cultivar has averaged approximately 20 days after that of the 'Payne' cultivar (non-patented in the United States). It has not been determined whether the time of leafing of the new cultivar will shift as the tree further matures. The typical leaf coloration is moderate olive green, 7.5 GY 4/4 on the upper surface and 5 GY 5/6 on the under surface. The typical sepal coloration is moderate olive green, 5 GY 4/4. The leaves are pinnately compound and approximately 40 cm in length and approximately 25 cm in width. The leaf margins are entire. The typical petiole coloration is 2.5 GY 6/8 strong yellow green, and the typical leaf vein coloration is 2.5 GY 6/8 strong yellow green. The petioles commonly are approximately 11 cm in length to the first leaflet and 30 cm in length to the base of the terminal leaflet. The typical petiole diameter is approximately 3.5 mn.

Inflorescence: The new cultivar has proven to be relatively precocious. First bloom has occurred at an age of 3 years or 4th leaf. From 1995 to 1998 first bloom has occurred on young trees of the new cultivar on April 21 on average, peak bloom on April 26th on average, and last bloom on May 1st on average. For comparative purposes the 'Chandler' cultivar from 1988 to 1998 exhibited first bloomed on April 15th on average, peak bloom on April 22nd on average, and last bloom on April 29th on average. It has not been determined whether the time of blooming of the new cultivar will shift as the tree further matures. The flowers a typical of *Juglans regia* in number and shape with two flowers per inflorescence borne at both the terminal and lateral positions on the current year's growth. This makes possible increased yields over walnut cultivars that bear fruit terminally. A typical flower diameter is approximately 5 to 7 mm at anthesis. The floral organs are typical of *Juglans regia*. The flower fragrance is typical of *Juglans regia* and is not noticeably different than the foliage fragrance. Approximatley 90 percent of the lateral buds are fruitful.

Walnuts: The new cultivar commonly harvests prior to the 'Chandler' cultivar. During 1998 young trees of the new cultivar were ready for harvest on October 2nd. This compares to October 12th for the 'Chandler' cultivar during 1998. Jumbo-sized walnuts are formed in good yield which exhibit a flavor typical of commercial walnut cultivars. The nutshell is 10 YR 5/6 strong yellowish brown in coloration. As illustrated in FIGS. 4 and 5, the kernels display a distinctive red-purple pellicle which can be used to readily distinguish the new cultivar. Such coloration typically approaches 41–42 of the Munsell color scale. The new cultivar is regular bearing (not alternate bearing). However, as will be apparent to those skilled in walnut production, the size of the walnuts that are produced will vary somewhat with the yield achieved during a given growing season. During the current growing season the walnuts averaged approximately 36.4 mm. in length and approximately 35.8 mm. in width. The shell is strong, thick, and well-filled and the kernel is easy to remove. The kernel commonly weighs approximately 7.1 g. on average and commonly consists of approximately 48 percent by weight on average of the average total walnut weight of approximately 14.8 g. These values are based upon four year averages of ten walnut samples obtained from young trees and are considered to be fairly typical of commercial walnuts. The walnut yield is good but tends to be lower than that of the 'Chandler' cultivar during observations to date. Typical kernel dimensions are approximately 28 mm in length and approximately 29 mm in width.

Hardiness: Trees have withstood temperatures of 21° F. in late December.

Disease resistance and suseptibility: Susceptibility to walnut blight *Xanthomonas campestris* var. *juglandis* damage is average. Susceptibility to mite damage is greater than average. No other unusual resistance or susceptibility to insects or diseases has been observed to date.

Usage: The new cultivar of the present invention provides distinctive kernels having a naturally-occurring festive red-purple appearance that are particularly suited for consumption at parties, holidays, or other special occasions.

We claim:

1. A new and distinct cultivar of *Juglans regia* tree having the following combination of characteristics:

(a) forms jumbo-sized walnuts with little size variation in a given harvest which possess strong thick well-filled shells and easy to remove kernels, (b) forms kernels which display a distinctive red-purple pellicle, (c) bears fruit laterally, and (d) yields a walnut crop that commonly can be harvested from a young tree prior to that of the 'Chandler' cultivar (U.S. Plant Pat. No. 4,388) at Davis, Calif.;

substantially as herein illustrated and described.

* * * * *